(12) United States Patent
Han et al.

(10) Patent No.: US 7,807,420 B2
(45) Date of Patent: Oct. 5, 2010

(54) METHOD FOR RECOVERING A BASIC AMINO ACID FROM A FERMENTATION LIQUOR

(75) Inventors: Duck-Keun Han, Gunsan (KR); Jong-Kyu Choi, Jeonju (KR); Il-Kwon Hong, Gunsan (KR); Hyun-Ho Kim, Gunsan (KR); Jong-Soo Choi, Gangseo-Gu (KR); Tae-Hui Kim, Gunsan (KR); Sung Hyun Kim, Gunsan (KR)

(73) Assignee: Paik Kwang Industrial Co., Ltd., Jeollabuk-Do (KR)

( * ) Notice: Subject to any disclaimer, the term of this patent is extended or adjusted under 35 U.S.C. 154(b) by 495 days.

(21) Appl. No.: 11/918,356

(22) PCT Filed: Apr. 13, 2006

(86) PCT No.: PCT/EP2006/003431

§ 371 (c)(1),
(2), (4) Date: Oct. 12, 2007

(87) PCT Pub. No.: WO2006/108663

PCT Pub. Date: Oct. 19, 2006

(65) Prior Publication Data

US 2009/0075348 A1    Mar. 19, 2009

(30) Foreign Application Priority Data

Apr. 15, 2005 (DE) .................. 10 2005 017 507

(51) Int. Cl.
C12P 13/08 (2006.01)
C12P 13/04 (2006.01)
C12P 13/10 (2006.01)
C12P 13/24 (2006.01)

(52) U.S. Cl. .................. 435/115; 435/106; 435/107; 435/114

(58) Field of Classification Search .................. None
See application file for complete search history.

(56) References Cited

U.S. PATENT DOCUMENTS 4,714,767 A    12/1987 Tanaka et al.
4,997,754 A *  3/1991 Miyazawa et al. .......... 435/106
5,017,480 A *  5/1991 Mori et al. ................ 435/106
2009/0054685 A1* 2/2009 Murata et al. ............. 562/554

FOREIGN PATENT DOCUMENTS

EP    1 106 602 A1    6/2001
JP    62-255452 A     11/1987
JP    62-255453 A     11/1987

OTHER PUBLICATIONS

Atkinson, B., et al., "Industrial Microbial Processes," *Biochemical Engineering and Biotechnology Handbook*, Second Edition, Stockton Press, Chapter 20, (1991), pp. 1111-1220.
Hsiao, T., et al., "Water Reuse in the L-Lysine Fermentation Process," *Biotechnology and Bioengineering*, vol. 49, (1996), pp. 341-347.
Kleemann, A., et al., "Amino Acids," *Ullmann's Encyclopedia of Industrial Chemistry*, 5th Edition, vol. A2, (1997), pp. 57-97.
Lee, I., et al., "The Use of Ion Exclusion Chromatography As Approved to the Normal Ion Exchange Chromatography to Achieve a More Efficient Lysine Recovery From Fermentation Broth," *Enzyme and Microbial Technology*, vol. 30, (2002), pp. 798-803.
Pfefferle, W., et al., "Biotechnological Manufacture of Lysine," *Advances in Biochemical Engineering/Biotechnology*, vol. 79, (2003), pp. 59-112.
Hermann, T., "Industrial Production of Amino Acids by Coryneform Bacteria," *Journal of Biotechnology*, vol. 104, (2003), pp. 155-172.

* cited by examiner

*Primary Examiner*—Herbert J. Lilling
(74) *Attorney, Agent, or Firm*—McCarter & English, LLP; Elizabeth A. Hanley, Esq.; Maneesh Gulati, Esq.

(57) ABSTRACT

The invention relates to a method for recovering a basic amino acid from the fermentation liquor of a micro-organism strain that produces the basic amino acid. The method comprises the following steps: a) isolation of the micro-organisms from the fermentation liquor and b) separation of the basic amino acid from the aqueous liquor that has been obtained in step a) by the successive charging of a single or multiple stage arrangement of a strongly acidic cation exchanger in the form of a salt with the liquor obtained in step a) and the elution of the basic amino acid. According to the invention, prior to the charging process in step b), the aqueous liquor has a pH value ranging between 4 and 7.5 and at least the first stage of the carbon exchanger arrangement is pre-treated with an aqueous acid in such a way that at the end of said pre-treatment, the pH value at the discharge of the pre-treated cation exchanger ranges between 4.5 and 7.

20 Claims, 2 Drawing Sheets

ADSORPTION

DESORPTION

METHOD FOR RECOVERING A BASIC AMINO ACID FROM A FERMENTATION LIQUOR

RELATED APPLICATIONS

1. Field of the Invention

This application is a national stage application under 35 U.S.C. 371 of PCT/EP2006/0034631, filed Apr. 13, 2006, which claims priority to German application 10 2005 017 507.4, filed Apr. 15, 2005.

The present invention relates to a method for producing a basic amino acid from the fermentation broth of a microorganism strain producing the basic amino acid.

2. Background of the Invention

Basic amino acids such as L-lysine, L-histidine, L-arginine and L-ornithine are predominantly produced by microbial fermentation methods (see e.g. Axel Kleemann et al., "Amino acids", in "Ullmann's Encyclopedia of Industrial Chemistry", 5th Edition on CD-ROM, 1997 Wiley-VCH and literature cited there; Th. Hermann, J. Biotechnol. 104 (2003), pp. 155-172 and literature cited there; Pfefferle et al., Adv. Biochem. Eng./Biotechnology, Vol. 79 (2003), 59-112 and literature cited there, and also Atkinson et al., in Biochemical Engineering and Biotechnology Handbook, 2nd ed., Stockton Press, 1991, Chapter 20 and literature cited there).

In the case of such fermentation methods, primarily an aqueous fermentation broth is obtained which, in addition to the desired basic amino acid and the biomass resulting from the microorganisms used, comprises a multiplicity of byproducts and impurities, e.g. other amino acids, substrate residues, salts, products of cell lysis and other byproducts.

The production of basic amino acids from the fermentation broth, and its purification are frequently performed using strongly acidic cation exchangers (see e.g. Th. Hermann, loc. cit; Atkinson et al, loc. cit.). For this purpose, the aqueous fermentation broth, before or after removing the microorganisms and other insoluble constituents (biomass), is acidified with a strong acid, for example sulfuric acid, to a pH below 2, so that the basic amino acid is present as dication. The acidified aqueous broth is then passed through a strongly acidic cation exchanger, the acid groups of which are present in the salt form, e.g. as sodium or ammonium salts, as a result of which the dication of the basic amino acid is adsorbed to the ion-exchange resin. Thereafter, the cation exchanger loaded with the basic amino acid is washed usually with water to remove impurities. The basic amino acid is then eluted by treatment with a dilute aqueous base, for example sodium hydroxide solution, ammonia water or an aqueous ammonium buffer, the salt form of the cation exchanger being regenerated at the same time. From the eluate thus produced, the basic amino acid, if appropriate after acidifying the eluate, is isolated in a conventional manner, e.g. by crystallization.

Of course, the liquid (effluent) flowing off when the cation exchanger is being loaded with the dication of the basic amino acid has a high salt loading and can therefore be termed high density waste water (HDWW). Also, the, if appropriate, succeeding wash step produces large amounts of water having a salt loading (low density waste water (LDWW)). These waste waters, to decrease the salt loading, must be subjected to complex waste water treatment. Alternatively, the salty waste waters can be dewatered and the resultant concentrate can be disposed of or fed to another use. However, both measures are associated with additional expenditure in terms of apparatus and high energy consumption and therefore contribute to a not inconsiderable extent to the costs of the fermentative amino acid production. There has therefore been no lack of attempts to reduce the salt loading and the amount of waste water which are produced in a workup by cation exchangers of fermentation broths comprising basic amino acid.

Hsiao et al., Biotechnology and Bioengineering Vol. 49 (1996) pp. 341-347 propose, to reduce the amount of waste water, recirculating, to the fermentation medium, the salty effluents produced at the cation exchanger. In addition to the risk that as a result fermentation inhibitors which are customarily formed as byproducts in the metabolism of the microorganisms accumulate in the fermentation medium, it has been found that in this case the binding capacity of the cation exchanger is decreased so that the cost savings achieved by the reduced amount of waste water are consumed by the costs of a larger cation exchange arrangement.

I. Lee et al., Enzyme and Microbiol. Technol. 30 (2002) pp. 798-803, to reduce the salt loading in the workup of lysine-containing fermentation broths, propose the use of ion-exclusion chromatography instead of the cation exchanger customarily used. For this, first the solids content of the fermentation broth is removed by means of microfiltration. The resultant aqueous lysine-containing broth is adjusted to the isoelectric point (pH 9.74) and then passed through a cation exchanger. Since the ionic constituents of the broth are not absorbed, these are recovered in the effluent. The amino acid is then eluted with water. However, it has been found that a high recovery rate of L-lysine of greater than 90% is only achieved when not only is the rate of lysine-containing feed low, but also the through-flow rate. Despite the lower salt loading, therefore, this embodiment is not economic.

U.S. Pat. No. 4,714,767 on the other hand describes a multistage method for separating off basic amino acids from an aqueous broth by means of an arrangement of a plurality of series-connected cation-exchange columns in which the last part of the effluent produced on loading the first column is recirculated to the loading operation of a later separation. It is also proposed that the last part of the eluate of the first column is recirculated to the elution process of a later separation. In this manner the amount of water is reduced, but not the salt loading.

EP 1,106,602 A1 describes the separation of amino acids from impurity-containing aqueous solutions of the amino acids by simulated moving bed chromatography on a strongly acidic cation exchanger. According to a preferred embodiment, for this an apparatus is used which comprises one or more series-connected chromatography columns having a strongly acidic cation exchanger and which comprises, in a sequential arrangement, a first desorption port, an extract port, a feed port, a raffinate port and a second desorption port. To separate off the amino acid, simultaneously (i) via the feed port, an amino acid-containing feed solution and (ii) via the first desorption port, a basic eluant, are brought into contact with the cation exchange material, if appropriate (iii) an aqueous solution is taken off via the second desorption port, and (iv) via the extract port a solution is taken off which comprises the amino acid and, compared with the feed solution, has a lower amount of impurities. Advantages with respect to reduction of the salt loading and the amount of waste water are not clear.

DETAILED DESCRIPTION OF THE INVENTION

Figure 1A:
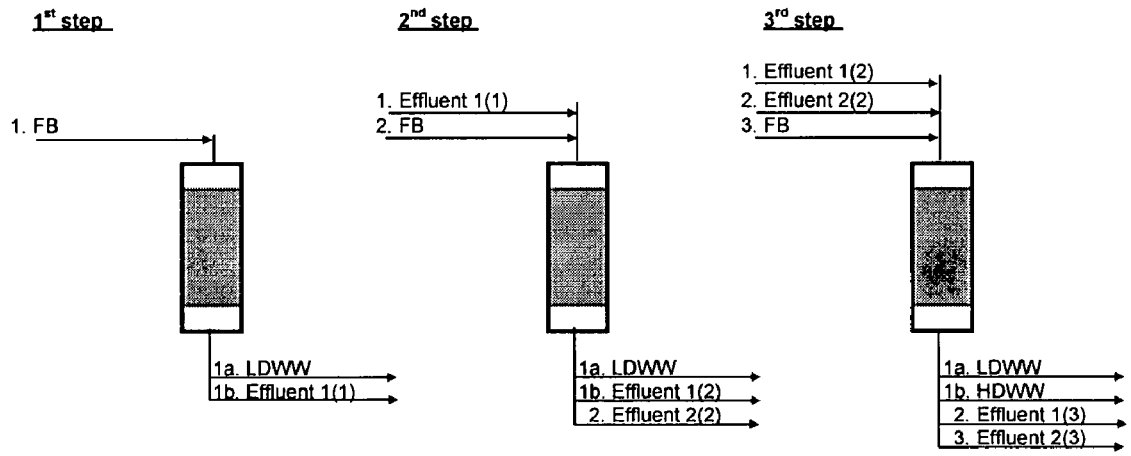
FIG. 1a depicts the individual effluents of the startup process of the present invention. First, the broth FB obtained after separating off the biomass is passed through the cation-exchange arrangement (shown diagrammatically). The first portion of the effluent is termed LDWW (low density waste water) and corresponds to the "free volume" of the ion exchanger; the second portion of the effluent is collected as effluent 1(1). The cation-exchange arrangement is then again charged with effluent 1(1). The first portion of the effluent is taken off as LDWW, and the second portion is taken off as effluent 1(2). Subsequently, loading with broth FB is carried out, the effluent of which is taken off as effluent 2(2). In the next step, the cation-exchange arrangement is charged in the sequence effluent 1(2), effluent 2(2), broth FB. During charging with the effluent 1(2), at the outlet, in addition to LDWW, HDWW also arises.

The object therefore underlying the present invention is to provide a method for producing basic amino acids from the fermentation broth of a microorganism strain producing the basic amino acid, which method overcomes the disadvantages described of the prior art.

It has surprisingly been found that this object is achieved by a method in which, first, the majority of the microorganism is separated off from the fermentation broth (step a) and then the basic amino acid is separated off from the resultant aqueous broth by successive loading of a singlestage or multistage, generally serial arrangement of a strongly acidic cation exchanger in its salt form with the broth, and eluting the basic amino acid (step b), when the basic broth, before loading, has a pH in the range from 4.0 to 7.5, in particular 4.5 to 7.2, and especially 4.6 to 7, and at least the first stage of the cation-exchange arrangement is pretreated with an aqueous acid in such a manner that at the end of the pretreatment the pH in the effluent of the pretreated cation exchanger is in the range from 4.5 to 7.0.

Accordingly, the present invention relates to the method presented here and in the claims for producing a basic amino acid from the fermentation broth of a microorganism strain producing the basic amino acid.

The inventive method is associated with a number of advantages: firstly, the amount of salt produced in the inventive method, and thus the salt loading of the waste water, are lower than in the methods of the prior art in which cation exchangers are used to separate off and produce the basic amino acid from the fermentation broth. In addition, high yields of generally greater than 95% of basic amino acid are achieved even at high loadings and through-flow rates at the cation exchanger. On account of the selected pHs of the broth, there is no occurrence of significant precipitation of impurities which can block the cation exchanger and therefore would increase the wash water requirement.

According to the invention, in a first step, the majority of the microorganisms present in the fermentation broth and, if appropriate, other solids present, are separated off from the fermentation broth. Complete separation of these constituents is not necessary in principle. Customarily, however, at least 70%, and in particular at least 80%, of the solids present in the fermentation broth, including microorganisms, are separated off in step a). Preferably, the resultant aqueous broth comprises less than 1% by volume, and in particular no more than 0.6% by volume, of cell materials.

The separation of the microorganisms and other solid constituents can be performed in customarily for the separation of microorganisms by filtration including cake- and depth-filtration, cross-flow filtration, by membrane separation methods such as ultra- and microfiltration, by centrifugation and decanting, by using hydrocyclones, a combination of the methods cited, or in another manner.

Before the separation, it has proved to be useful to inactivate the microorganisms in the fermentation broth (sterilizing the fermentation broth), for example by customary pasteurization methods, e.g. by introducing heat and/or hot steam. For this, conventional heat exchangers, for example shell-and-tube heat exchangers or plate heat exchangers can be used.

The broth obtained after separating off the majority of microorganisms and, if appropriate, other solids, customarily has a content of basic amino acid of from 4 to 30% by weight, frequently 8 to 20% by weight, and in particular 10 to 15% by weight. The pH is frequently in the range from 5 to 7.5, and in particular in the range from 6 to 7. Therefore, adjustment of the pH of the aqueous broth, e.g. acidification as in the prior art, can be omitted. In principle, however, it is possible to set the pH in the above specified ranges, for example by adding small amounts of an acid, preferably an acid having a $pK_a<4.5$, such as formic acid, acetic acid, or sulfuric acid. In this embodiment, therefore, the broth preferably has a pH in the range from 4.0 to 6, in particular 4.5 to 5.5.

From the resultant aqueous broth, then, in step b), the basic amino acid is separated off using a cation exchange arrangement. The separation in step b) comprises according to the invention at least one pretreatment step, a subsequent loading step, in which the basic amino acid is adsorbed to the strongly acidic ion exchanger, and at least one elution step, by which the basic amino acid is desorbed from the ion exchanger. These steps can be repeated several times in the stated sequence and, between the steps, wash steps with water can be carried out.

The cation exchange arrangement used in the inventive method comprises one or preferably more, e.g. 2, 3, 4 or more, up to 50, series-connected (serially connected) stages, customarily in the form of ion exchange columns which, as stationary phase, comprise one or more strongly acid cation exchangers.

As strongly acidic cation exchangers, in principle all ion-exchange materials, e.g. organic ion-exchange resins or inorganic ion exchangers, come into consideration which have strongly acidic groups, generally sulfonate groups. Frequently, these are particulate, moderately or greatly crosslinked organic polymers, frequently based on polystyrene, which have on the surface of the polymer particles a multiplicity of strongly acidic groups. The mean number of acidic groups is customarily in the range from 1 to 4 meq/ml of ion-exchange resin. The mean particle size of the ion-exchange particles is typically in the range from 0.1 to 1 mm, with larger and also smaller particle sizes also being able to be suitable depending on the dimensioning of the ion-exchange arrangement. The polymer particles can be, for example, gel-like or have a macroporous structure.

Such ion exchangers are known and some are offered commercially for purifying amino acids, for example under the tradenames LEWATIT® K or LEWATIT® S from Bayer Aktiengesellschaft, e.g. LEWATIT® K 2629, LEWATIT® S110, LEWATIT® S110H, LEWATIT® S1467, LEWATIT® S1468, LEWATIT® S2568, LEWATIT® S2568H, AMBER-JET®, AMBERLYST® or AMBERLITE® from Rohm & Haas, e.g. Amberjet® 1200, AMBERJET® 1500, AMBER-LITE® 200, AMBERLITE® 250, AMBERLITE® IRV120, AMBERLITE® IR 120, AMBERLITE® IR 200C, AMBER-LITE® CG 6000, AMBERLYST® 119 Wet, DOWEX® from Dow Chemicals, e.g. DOWEX® 50X1-100, DOWEX® 50X2-100, DOWEX® 50X2-200, DOWEX® 50X2-400, DOWEX® 50X4-100, DOWEX® 50X4-200, DOWEX® 50X4-400, DOWEX® 50X8-100, DOWEX® 50X8-200, DOWEX® 50X8-400, DOWEX® 40X1-100, DOWEX® 40X1-100, DOWEX® 40X1-100, DOWEX® HCR-S DOWEX® HCR-W2, DOWEX® MSC-1, DOWEX® 650C, DOWEX® G26, DOWEX® 88, DOWEX® Monosphere 88, DOWEX® Monosphere 99K/320, DOWEX® Monosphere 99K/350, DOWEX® Monosphere 99Ca/320, DOWEX® Marathon C, DOWEX® 032, DOWEX® 406, DOWEX® 437, DOWEX® C500ES, DOWEX® XUS 43518, DOWEX® XUS 40406.00, DIAION® from Mitsubishi Corp., e.g. DIAION® SK1B, DIAION® SK1BS, DIAION® SK104, DIAION® SK112, DIAION® SK116, DIAION® 1-3561, DIAION® 1-3565, DIAION® 1-3570, DIAION® 1-3573, DIAION® 1-3577, DIAION® 1-3581, DUOLITE® D 5427, DUOLITE® D 5552 (organically based cation exchanger), and in addition ADSORBOSPHERE® SCX, BAKERBOND® SCX, PARTISIL® SCX, SPHERISORB® SCX, SUPELCOSIL® LC3-SCX, ULTRALSIL® SCX and ZORBAX® 300 SCX (silica-based cation exchanger).

The cation-exchange arrangement can be operated batchwise and then has one or more, e.g. 2, 3 or 4, series-connected (serially connected) stationary ion-exchange fixed beds. It can also be operated continuously and then has generally 5 to 50, and in particular 15 to 40, ion-exchange beds, which can be, e.g., constituent of a "true moving bed" arrangement (see K. Tekeuchi J. Chem. Eng. Japan 11 (1978 pp. 216-220), a "continuous circulating annular" arrangement (see J. P. Martin, Discuss. Farraday Soc. 1949, p. 7) or of a "simulated moving bed" arrangement, as described in, for example, U.S. Pat. No. 2,985,589, WO 01/72689 and also by G. J. Rossiter et al. Proceedings of AIChE Conference, Los Angeles, Calif., November 1991, or H. J. Van Walsem et al. J. Biochtechnol. 59 (1997) pp. 127-123.

Before the inventive pretreatment of the cation exchanger with the aqueous acid, the cation exchanger is in its salt form, i.e. the strongly acidic groups of the cation exchanger are in deprotonated form and coordinate to give charge neutrality to a corresponding number of cations. Generally, the cations are alkali metal cations, in particular sodium ions or, particularly preferably, ammonium ions ($NH_4^+$).

As a result of the inventive pretreatment with the weak aqueous acid, a portion of these cations are eluted and an equivalent number of the acidic groups are reprotonated, so that on the cation exchanger, not only acidic, but also basic, groups are present. It is assumed that as a result the binding capacity of the ion exchangers for the basic amino acid is increased and thus the capacity of the ion exchange arrangement is increased. The process of elution/reprotonation can be monitored via the pH of the aqueous liquid flowing off at the cation exchanger during the pretreatment. According to the invention, the desired degree of pretreatment is achieved when the pH of the effluent liquid (determined at 25° C.) is in the range from 4.5 to 7, and in particular in the range from 5 to 6.6.

For the pretreatment, in principle dilute solutions of all known aqueous acids can be used. Of course, these acids are preferably selected in such a manner that they do not interfere with the production of the basic amino acid from the eluate. If the acid is an acid other than the basic amino acid to be isolated, those acids are preferred which are not adsorbed by the cation exchanger or are only adsorbed to a very slight extent. Those which are suitable are both inorganic acids such as sulfuric acid, hydrochloric acid, nitric acid and phosphoric acid, organic carboxylic acids having preferably 1 to 4 carbon atoms such as formic acid, acetic acid, propionic acid, polycarboxylic acids having generally 2 to 4 carboxyl groups and if appropriate hydroxyl groups such as maleic acid, fumaric acid, succinic acid, adipic acid, citric acid and the like, hydroxycarboxylic acids such as lactic acid and glycolic acid, and sulfonic acids, and also, in protonated form, the amino acids to be isolated, e.g. the mono- and dications of the abovementioned basic amino acids. Preferred acids are firstly acids having a $pK_a<4$, in particular formic acid and sulfuric acid, and secondly the basic amino acid to be isolated, in the form of its monocation.

The concentration of acid in the aqueous solution is customarily in the range from 1 to 85 g/l, in particular in the range from 2 to 40 g/l. When this is an acid which is different from a basic amino acid, the amount of acid required to achieve the desired effect is customarily from 0.01 to 0.2 mol/l of cation exchanger, in particular from 0.02 to 0.1 mol/l of cation exchanger. If the acid used for the pretreatment is a basic amino acid, e.g. the basic amino acid to be isolated, the amount of acid is preferably from 0.3 to 1.2 mol/l, and in particular from 0.5 to 0.8 mol/l of cation exchanger. The amount of aqueous acid solution is customarily 0.7 to 10 times the total bed volume of the cation exchange arrangement.

The specific flow rate SV, i.e. the ratio of mean flow rate V (volumetric rate) at which the aqueous acid is passed through the cation-exchange arrangement, to the total volume of cation exchanger in the cation-exchange arrangement (bed volume BV), is of minor importance and is typically in the range from 0.1 to 5 $h^{-1}$. The temperature at which the treatment is performed is typically in the range from 10 to 80° C., preferably in the range from 20 to 70° C., and in particular in the range from 30 to 60° C. The treatment can be carried out not only in an ascending manner, i.e. the aqueous acid solution is passed from bottom to top through the column(s) of the cation-exchange arrangement, but also in a descending manner, i.e. the aqueous acid solution is passed from top to bottom through the column(s) of the cation-exchange arrangement.

The cation exchanger thus pretreated is then loaded with the basic amino acid by passing the aqueous broth freed from the biomass through the cation-exchange arrangement. The loading can be performed not only in a descending manner but also ascending manner, with the former being preferred. The loading is preferably performed at a specific flow rate in the range from 0.1 $h^{-1}$ to 2 $h^{-1}$. The loading is preferably performed at a temperature in the range from 20 to 70° C., and in particular in the range from 30 to 60° C. The amount of aqueous broth is customarily selected so that at least 60%, and in particular at least 65%, of the basic amino acid present in the aqueous broth is adsorbed. The amount of aqueous broth is generally 0.5 to 2 times the amount of the bed volume. Depending on the degree of adsorption, the effluent at the exit of the cation-exchange arrangement still comprises the basic amino acid, so that the effluent, if appropriate after adjusting the pH, can be used for the pretreatment according to embodiment A or B. Customarily, however, pH adjustment is not necessary.

The loading process can be followed by a wash step. For this, water, e.g. process water, is passed through the cation-exchange arrangement. The amount of wash water is, at this stage, customarily 0.05 to 0.3 times the bed volume. The resultant wash waters customarily comprise impurities and are discarded. They can also comprise small amounts of the basic amino acid and can then be combined with the effluent produced on loading.

The loading step, or the wash step carried out if appropriate, is followed by the elution of the basic amino acid. For this, an aqueous solution of a base (eluant) is passed through the cation-exchange arrangement. As a result the basic amino acid is desorbed and is eluted, and the cation exchanger is regenerated, i.e. the acidic groups of the cation exchanger are converted back to the salt form. The base concentration in the eluant is customarily in the range from 1 to 10% by weight, and in particular in the range from 2 to 8% by weight. Suitable bases are, for example, ammonia, alkali metal hydroxides and alkali metal carbonates, with sodium hydroxide solution and, in particular, ammonia being preferred. The amount of aqueous base is generally 0.5 to 5 times the amount of the bed volume. With regard to the temperatures and flow rate, that said for loading applies. The elution can be carried out not only in the ascending but also descending manner. The elution is preferably carried out in the same direction as loading.

The elution can be followed by a further wash step, if appropriate to remove impurities present. For this, water is passed through the cation-exchange arrangement. The amount of wash water at this stage is customarily 0.2 to 1.3 times the bed volume. The effluent produced in the wash step is fed as waste water of low salt loading to a customary waste water treatment, or to another workup.

The eluate produced in the elution is worked up in a customary manner to produce the amino acid. Generally, for this, the eluate will be concentrated, e.g. by removing the water in a customary evaporator arrangement.

In this manner a concentrated aqueous solution of the basic amino acid is obtained, from which the basic amino acid can be isolated as hydrochloride, e.g., after addition of hydrochloric acid, by precipitation or crystallization. Methods for this are known to those skilled in the art and are extensively described in the literature (e.g. Hermann, T. Industrial Production of amino acids by coryneform bacteria, J. of Biotechnology, 104 (2003), 155-172).

The aqueous condensate produced in the concentration can be discarded or recirculated to the process. For example, the condensate can be recirculated to the elution step of the basic amino acid in a subsequent amino acid separation. Preferably, for this, the condensate, after the elution with the aqueous base, is passed through the cation-exchange arrangement. The resultant effluent frequently still comprises small amounts of basic amino acid and is customarily recirculated to the elution of a subsequent amino acid separation.

The invention will be described in more detail below with reference to two preferred embodiments.

In a first preferred embodiment (embodiment A) of the invention, for the pretreatment of the cation exchanger, use is made of an aqueous solution of the basic amino acid to be isolated which has a pH in the range from 4.5 to 7.5. Preferably, the aqueous solution has a concentration of basic amino acid in the range from 1 to 85 g/l, and in particular 2 to 40 g/l. The amount of basic amino acid required to achieve the desired effect is customarily 0.3 to 1.2 mol/l, and in particular 0.5 to 0.8 mol/l of cation exchanger. The amount of aqueous acid solution is preferably 0.7 to 10 times the total bed volume of the cation-exchange arrangement.

Expediently, as aqueous solution of the basic amino acid, use is made of at least one portion of the effluent of a loading of the cation-exchange arrangement from a preceding amino acid separation which comprises the non-absorbed basic amino acid. In the case of a multistage cation-exchange arrangement, the solution preferably comprises at least a portion, e.g. at least 50%, or the total amount, of the effluent of the first stage.

Of course, when the process according to embodiment A is carried out the first time, such an effluent is not yet present. Therefore, the cation-exchange arrangement must be started up in advance. For this, the aqueous broth obtained after separating off the biomass is passed through the cation-exchange arrangement, the cation exchanger being loaded with the basic amino acid. The resultant effluent customarily does not yet comprise adsorbed basic amino acid, and has a pH in the above-specified limits. The resultant effluent can then be used for pretreating the cation-exchange arrangement.

Figure 1B:
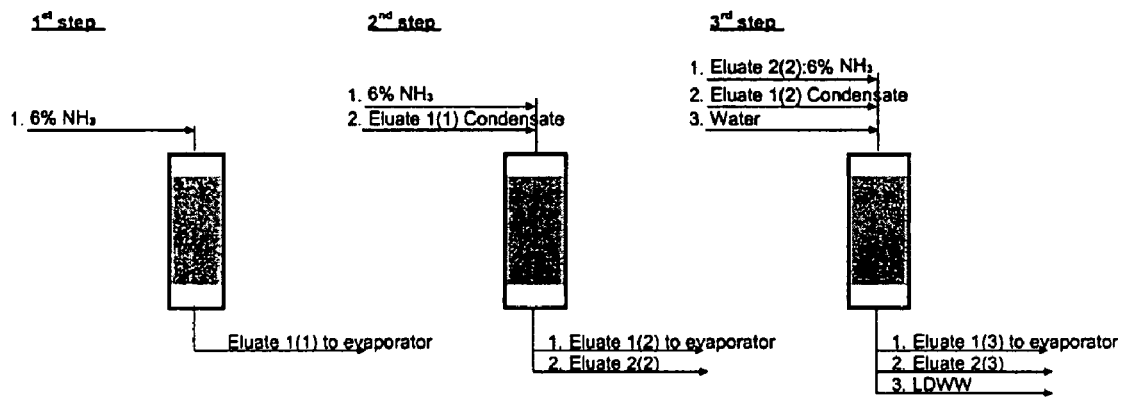
FIG. 1b depicts the subsequent elution with ammonia water (e.g., 6% $NH_3$). The resultant eluate 1 which comprises the basic amino acid is separated in an evaporator arrangement (not shown) into condensate and amino acid concentrate. It is again charged with ammonia water (e.g., 6% $NH_3$) (eluate 1(2) again results therefrom at the outlet) and then with the condensate of the evaporation step. The resultant effluent is termed eluate 2(2) and used for producing an ammonia water which is passed to the ion exchanger in the next step. The resultant eluate 1(2) is again separated into condensate and amino acid concentrate in an evaporator arrangement and the resultant condensate is again passed to the ion exchanger (effluent: eluate 2(3)). Then, to purify the cation-exchange arrangement it is washed with water and the effluent fed as LDWW to disposal or workup.

FIGS. 1a and 1b show the individual effluents of a preferred embodiment of the start-up process. First, the broth FB obtained after separating off the biomass is passed through the cation-exchange arrangement (shown diagrammatically). The first portion of the effluent is termed LDWW (low density waste water) and corresponds to the "free volume" of the ion exchanger; the second portion of the effluent is collected as effluent 1(1). The cation-exchange arrangement is then again charged with effluent 1(1). The first portion of the effluent is taken off as LDWW, and the second portion is taken off as effluent 1(2). Subsequently, loading with broth FB is carried out, the effluent of which is taken off as effluent 2(2). In the next step, the cation-exchange arrangement is charged in the sequence effluent 1(2), effluent 2(2), broth FB. During charging with the effluent 1(2), at the outlet, in addition to LDWW, HDWW also arises. After this, the elution with ammonia water (e.g. 6% $NH_3$) is performed. The resultant eluate 1 which comprises the basic amino acid is separated in an evaporator arrangement (not shown) into condensate and amino acid concentrate. It is again charged with ammonia water (e.g. 6% $NH_3$) (eluate 1(2) again results therefrom at the outlet) and then with the condensate of the evaporation step. The resultant effluent is termed eluate 2(2) and used for producing an ammonia water which is passed to the ion exchanger in the next step. The resultant eluate 1(2) is again separated into condensate and amino acid concentrate in an evaporator arrangement and the resultant condensate is again passed to the ion exchanger (effluent: eluate 2(3)). Then, to purify the cation-exchange arrangement it is washed with water and the effluent fed as LDWW to disposal or workup.

Figure 2:
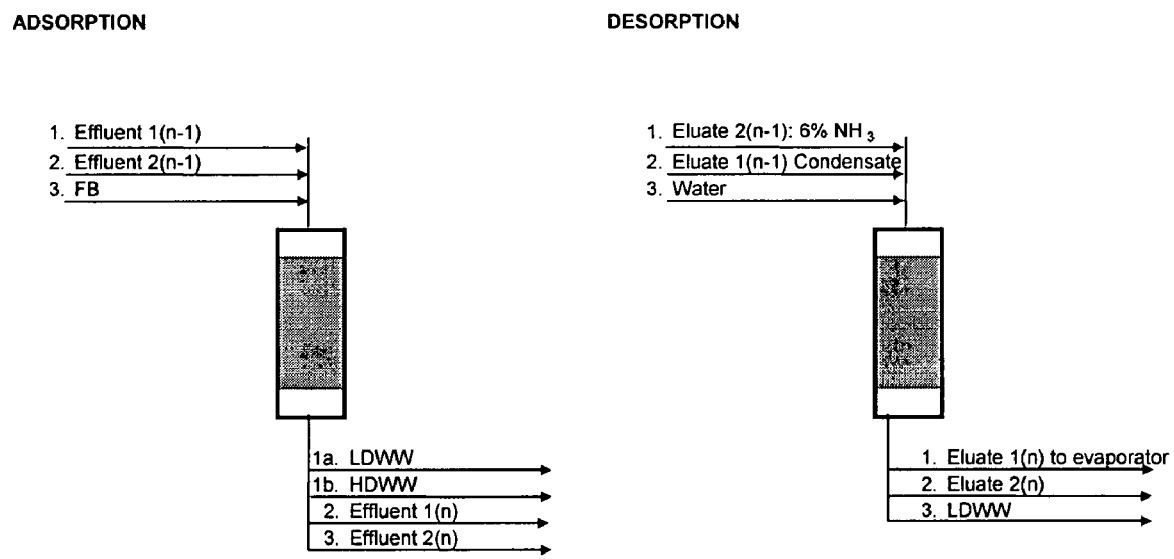
FIG. 2 depicts the individual effluents of preferred design of the embodiment A. First, effluent 1 of the start-up process (or effluent 1(n−1) of a preceding procedure of embodiment A) is passed through the cation-exchange arrangement and the resultant effluent is fed as LDWW and then HDWW to disposal or workup. Then, effluent 2 of the start-up process (or effluent 2(n−1) of a preceding procedure of embodiment A) is passed through the cation-exchange arrangement. The effluent is collected as effluent 1(n) and fed at the point of the amino acid separation corresponding to the effluent 1(n+1) in a following stage. Thereafter, the aqueous broth FB obtained after separating off the biomass from the fermentation broth is passed through the cation-exchange arrangement. The effluent is collected as effluent 2(n) and is fed at the point of the amino acid separation corresponding to the effluent 2(n+1) in a following stage. Thereafter the elution is performed using the eluate 2(n−1) resulting from the start-up process, or from the preceding stage, which eluate has been made up to 6% ammonia water. From this results eluate 1(n) which is separated in an evaporator arrangement (not shown) into condensate and amino acid concentrate. The condensate is fed to the following stage. As a further elution step, the condensate of the start-up process, or the preceding stage, eluate 1(n−1), is applied to the ion exchanger and the effluent is collected as eluate 2(n) and made up to 6% strength ammonia water for the following stage. Then, for purification of the cation-exchange arrangement, it is washed with water and the effluent is fed as LDWW to disposal or workup.

FIG. 2 shows the individual effluents of preferred design of the embodiment A. First, effluent 1 of the start-up process (or effluent 1($n-1$) of a preceding procedure of embodiment A) is passed through the cation-exchange arrangement and the resultant effluent is fed as LDWW and then HDWW to disposal or workup. Then, effluent 2 of the start-up process (or effluent 2($n-1$) of a preceding procedure of embodiment A) is passed through the cation-exchange arrangement. The effluent is collected as effluent 1($n$) and fed at the point of the amino acid separation corresponding to the effluent 1($n+1$) in a following stage. Thereafter, the aqueous broth FB obtained after separating off the biomass from the fermentation broth is passed through the cation-exchange arrangement. The effluent is collected as effluent 2($n$) and is fed at the point of the amino acid separation corresponding to the effluent 2($n+1$) in a following stage. Thereafter the elution is performed using the eluate 2($n-1$) resulting from the start-up process, or from the preceding stage, which eluate has been made up to 6% ammonia water. From this results eluate 1($n$) which is separated in an evaporator arrangement (not shown) into condensate and amino acid concentrate. The condensate is fed to the following stage. As a further elution step, the condensate of the start-up process, or the preceding stage, eluate 1($n-1$), is applied to the ion exchanger and the effluent is collected as eluate 2($n$) and made up to 6% strength ammonia water for the following stage. Then, for purification of the cation-exchange arrangement, it is washed with water and the effluent is fed as LDWW to disposal or workup.

In a second preferred embodiment B of the invention, for the pretreatment of the cation exchanger, use is made of a dilute aqueous solution of an acid, the $pK_a$ of which is no more than 4. Preferred acids are formic acid, phosphoric acid, hydrochloric acid, and in particular sulfuric acid, and also mixtures of these acids.

Preferably, the dilute aqueous acid solution has an acid concentration in the range from 1 to 20 g/l. The amount of acid required to achieve the desired effect is customarily 0.01 to 0.1 mol per liter of cation exchanger. The amount of aqueous acid solution is preferably 0.7 to 2 times the total bed volume of the cation-exchange arrangement.

In a preferred design of embodiment B, after the treatment with the dilute aqueous acid solution, a treatment with a dilute aqueous solution of the basic amino acid is carried out, in which solution at least 90% of the basic amino acid is present in a singly-protonated form. This solution customarily has a pH in the range from 4.5 to 7. Preferably, the aqueous solution has a concentration of basic amino acid in the range from 8 to 70 g/l, and in particular 8 to 50 g/l. The amount of aqueous solution of the basic amino acid is preferably 0.1 to 1 timer the total bed volume of the cation-exchange arrangement.

In a further preferred design of the embodiment B, first a treatment is carried out with only a portion of the dilute aqueous solution of the acid having a $pK_a \leq 4$ and then a treatment is carried out using a dilute aqueous solution of the basic amino acid in which at least 90% of the basic amino acid is present in singly-protonated form. With respect to concentration and pH, that stated above applies similarly. The amount of aqueous solution of the basic amino acid is preferably 0.1 to 1 time the total bed volume of the cation-exchange arrangement. Expediently, here also, as aqueous solution of the basic amino acid, use is made of at least a portion of the effluent of a loading of the cation-exchange arrangement from a preceding amino acid separation which comprises the non-absorbed basic amino acid. Following the treatment with the aqueous solution of the basic amino acid, there then generally follows a treatment with the remaining amount of the dilute aqueous solution of acid having a $pK_a \leq 4$.

The effluents which are produced in the treatment of the cation-exchange arrangement of the embodiment B are generally fed to waste water treatment. With respect to the waste waters and recycling of eluents and condensates, that stated above for the embodiment A applies similarly.

The inventive method is applicable in principle to the isolation of all basic amino acids, in particular natural amino acids such as lysine, ornithine, histidine or arginine and is used, in particular, for isolating L-lysine produced by fermentation.

The type of the fermentation process and also of the microorganism strain used for producing the amino acid play no role for the inventive method, so that the inventive method is suitable for isolating the basic amino acid from any desired fermentation broths.

Generally, it is a method in which a microorganism strain which produces the desired basic amino acid is cultured in a fermentation medium which comprises, as substrate, at least one carbon source, e.g. molasses and/or raw sugar, and a nitrogen source, e.g. ammonia or ammonium salts such as ammonium sulfate, and also if appropriate minerals and trace elements. These substrate constituents can be used as such or in the form of a complex mixture, e.g. as corn-steep liquor.

The type of microorganism strain obviously depends on the type of amino acid to be produced. Generally, these are strains which overproduce the desired basic amino acid. In the case of L-lysine and histidine, these are generally strains of the genus *Corynebacterium* or *Brevibacterium*, e.g. of the species *Corynebacterium glutamicum* or *Brevibacterium lactofermentum*, in the case of arginine, strains of the species *Bacillus subtilis* or *Brevibacterium flavum*, with, however, recently strains of other species being used.

Generally, the fermentation is carried out until the content of basic amino acid in the fermentation broth is in the range from 50 to 200 g/l, and in particular in the range from 80 to 150 g/l. The content of biomass, i.e. microorganisms (as biodrymass) and other insoluble constituents of biological origin (e.g. cellulose fibers from the glucose source), is customarily in the range from 3 to 7% by weight. In addition, the fermentation broth generally further comprises residual amounts of substrate, e.g. unconsumed sugars, and also byproducts of fermentation, e.g. acidic or neutral amino acids or other basic amino acids, peptides and the like.

The fermentation methods can be carried out continuously or batchwise as batch or fed-batch methods. Generally, the methods relate to a fermentation broth which was produced by a fed-batch method, i.e. the majority of the substrate is fed to the microorganism-containing broth in the course of the fermentation.

Such methods and suitable microorganism strains are known to those skilled in the art, e.g. from the prior art cited at the outset (see, in particular, Pfefferle et al. and Th. Herrmann, loc. cit), and also WO 95/16042, WO 96/06180, WO 96/16042, WO 96/41042, WO 01/09306, EP-A 175309, EP-A 327945, EP-A 551614, EP-A 837134, U.S. Pat. Nos. 4,346,170, 5,305,576, 6,025,165, 6,653,454, DE 253199, GB 851396, GB 849370 and GB 1118719 (production of L-lysine), EP-A 393708, GB 1098348, U.S. Pat. Nos. 3,668, 072, 3,574,061, 3,532,600, 2,988,489, JP 2283290, JP 57016696 (L-ornithine), U.S. Pat. Nos. 3,902,967, 4,086,137, GB 2084566 (arginine) U.S. Pat. Nos. 3,875,001 and 3,902,966 (histidine).

The measures for carrying out and controlling such fermentations technically are familiar to those skilled in the art and can be found in the relevant literature, for example Storhas (see above) and J. E. Bailey et al. Biochemical Engineering Fundamentals, 2nd ed. MacGraw-Hill 1986, Chapter 9.

The invention will be described by the following figures, and also examples and comparative examples which show preferred embodiments of the inventive method and are not to be understood as restricting.

FIGS. 1a and 1b: The individual method steps of the start-up process of embodiment A (FIG. 1a: loading; FIG. 1b: desorption) are shown.

FIG. 2: The individual method steps of embodiment A are shown diagrammatically.

Abbreviations Used:
FB: fermentation broth
HDWW: high density waste water
LDWW: low density waste water
ID: inner diameter
H: height
Lys-HCl: L-lysine monohydrochloride
BV: bed volume (volume of the cation exchanger in the arrangement)
SV: specific flow rate (flow velocity in 1 $[m^3{}_{Feed}/(m^3{}_{resin} h)]$, unit hereinafter abbreviated as $[h^{-1}]$)

Materials Used:
All experiments were carried out using an L-lysine-containing fermentation broth which was produced in a manner known per se by fermentation with *C. glutamicum*. The fermentation broth had a content of Lys-HCl of 110 to 130 g/l and a content of biomass (calculated as biodrymatter) of 2.5-3.5% by weight. The salt content was between 3 and 5% by weight.

Cation-exchange Arrangement
In comparative example 1 and examples 1, 2 and 6, as cation-exchange arrangement served a cylindrical column of dimensions 25 mm (ID)×1200 mm (H) which was loaded with 400 ml of a strongly acidic cation-exchange resin. As cation exchanger, use was made of a sulfonated crosslinked polystyrene of the gel type having a mean particle size of about 0.6 mm (LEWATIT® S 1468 from Bayer Aktiengesellschaft) and a total capacity >2 meq/ml. The cation-exchange arrangement was equilibrated before its use with 6% strength by weight aqueous ammonia.

In examples 3 and 4, a cation-exchange arrangement of the "simulated moving bed" type having 30 cylindrical columns of dimensions 33 mm (ID)×1000 mm (H) (type "L 100 C" from AST, USA), in which case the chambers were packed in total with 18 l of a strongly acidic cation exchanger (LEWATIT® S1468 type from Bayer Aktiengesellschaft).

In example 5, there served, as cation-exchange arrangement, a cylindrical column having dimensions 35 mm (ID)× 900 mm (H), which had been charged with 600 ml of a strongly acidic cation-exchange resin (LEWATIT® S 1468).

The cation-exchange arrangement used in example 7 comprised 9 series-connected cylindrical columns of dimensions 35 mm (ID)×900 mm (H), each of which were packed with 845 ml of a strongly acidic cation-exchange resin (DIAION® SK 1 B from Mitsubishi, Japan).

All ion-exchange arrangements were equilibrated with 6% strength by weight ammonia solution before their first use.

COMPARATIVE EXAMPLE 1

A fermentation broth having a lysine content of 12.5% by weight and a biomass content of 3% by weight (as biodrymatter) is acidified to a pH of 1.5 using 0.7 g of concentrated sulfuric acid per g of Lys-HCl. The acidified fermentation broth was then passed through the cation-exchange arrangement at a temperature of 45° C. The resultant effluent was collected and disposed of as HDWW. The cation-exchange arrangement was then washed with water. The resultant effluent was disposed of as LDWW. Subsequently, L-lysine was eluted with 6% strength by weight aqueous ammonia in an amount of 0.305 g of ammonia/g of Lys-HCl.

EXAMPLE 1

The fermentation broth was heated and steam-sterilized at a temperature of 45 to 70° C. The cell mass was then removed by a combination of centrifugation and decanting. The aqueous residue had a lysine concentration of 12.5% by weight. The pH of the supernatant was 6.5.

Next, a total of 2040 ml of aqueous lysine solution consisting of five different effluents from preliminary stages of a preceding lysine isolation having a lysine content of 0.36-8.45% w/v and a pH of 4.5-7.5 was passed, at a temperature of 50° C., ascending through the cation-exchange arrangement. The pH of the effluent at the end of the pretreatment was 5.8. 416 ml of the supernatant of the centrifugation were then passed at a temperature of 55° C., ascending, through the cation-exchange arrangement thus pretreated. The resultant effluent was used in one of the following examples for the pretreatment. Subsequent thereto, lysine was eluted using 600 ml of a 6% strength by weight aqueous ammonia solution descending. The resultant aqueous lysine solution can be crystallized in a conventional manner.

EXAMPLE 2

The procedure of example 2 was carried out in a similar manner to example 1, but in contrast to example 1, for the pretreatment, 1248 ml of aqueous lysine solution consisting of three different effluents from preliminary stages of a preceding lysine isolation having a lysine content of 0.28-3.3% w/v and a pH of 6.3-6.7 were passed from top to bottom through the cation-exchange arrangement and the subsequent loading with the supernatant of the centrifugation was likewise carried out in a descending manner. The pH of the effluent at the end of the pretreatment was 6.5.

EXAMPLE 3

The fermentation broth was heated and sterilized by introducing steam at 45 to 70° C. The cell mass was then separated by centrifugation. The resultant supernatant had a lysine concentration of 12.5% by weight, and a pH of 7.2.

For the pretreatment, 55.1 l of aqueous lysine solution having a lysine content of 0.36-8.45% w/v by weight and a pH of 4.5-7.5 were passed at a temperature of 55° C. and a flow rate of 5.5 l/h upward through the cation-exchange arrangement. The pH of the effluent at the end of the pretreatment was 5.8. Subsequently, 9 l of the supernatant obtained in the centrifugation were passed at a temperature of 55° C. and a flow velocity of 5.5 l/h upward through the cation-exchange arrangement. Subsequently, elution was performed downward at a temperature of 55° C. and a flow rate of 5.5 l/h using a total of 10.8 l of a 6% strength by weight aqueous ammonia solution.

EXAMPLE 4

Example 4 was carried out in a similar manner to example 3, but for the pretreatment only 33.7 l of aqueous lysine solution consisting of three different effluents from preliminary stages of a preceding lysine isolation were passed at a lysine content of 0.28-3.3% w/v at a pH of 6.3-6.7 downward through the cation-exchange arrangement. The pH of the effluent at the end of the pretreatment was 6.5. Loading was carried out downward using in total 10.8 l of the centrifugation supernatant.

EXAMPLE 5

The fermentation broth was sterilized by heating and introducing steam at 45 to 70° C. and then transferred to a centrifugal separator. In this manner an aqueous lysine-containing supernatant was obtained having a lysine content of 118.3 g/l, a pH of 6.7, which still comprised 0.5% by volume cell material.

Through the cation-exchange arrangement were passed, at a temperature of 40 to 50° C. at a specific flow rate $SV=1\ h^{-1}$, successively 240 ml of a 0.44% strength by weight aqueous sulfuric acid, 500 ml of a 2,344% strength by weight aqueous lysine solution of a pH of 5 and then 180 ml of a 0.44% strength by weight aqueous sulfuric acid. The pH of the effluent was 5.2. Thereafter, at a flow rate of $SV=1\ h^{-1}$, while maintaining the temperature, 480 ml of the aqueous lysine-containing supernatant and then 120 ml of water were passed through the ion exchanger. The effluent was separated off and prepared for a pretreatment in a following step. Then, at an $SV=1\ h^{-1}$, at 55° C., 650 ml of a 4% strength by weight aqueous ammonia solution and then 720 ml of water were passed through the cation-exchange arrangement.

EXAMPLE 6

The fermentation broth was sterilized by heating and introducing steam at 45 to 70° C. and then transferred to a centrifugal separator. In this manner, an aqueous lysine-containing supernatant having a lysine content of 121 g/l, a pH of 6.7, which still comprised 0.5% by volume of cell material, was obtained.

Through the cation-exchange arrangement were passed, at a temperature of 40 to 50° C. at a specific flow rate SV=1.0, successively 160 ml of a 0.44% strength by weight aqueous sulfuric acid, 350 ml of a 1.23% strength by weight aqueous lysine solution of a pH of 5 and then 120 ml of a 0.44% strength by weight aqueous sulfuric acid. The pH of the effluent was 5.2. Thereafter, at an $SV=1\ h^{-1}$, while maintaining the temperature, 320 ml of the aqueous lysine-containing supernatant and then 80 ml of water were passed through the ion-exchange arrangement. The effluent was separated off and prepared for a pretreatment in a following step. Then, at an $SV=1\ h^{-1}$, at 55° C., 420 ml of a 4% strength by weight aqueous ammonia solution and then 480 ml of water were passed through the cation-exchange arrangement.

EXAMPLE 7

The fermentation broth was sterilized by heating and introducing steam at 45 to 70° C. and then transferred to a centrifugal separator. In this manner an aqueous lysine-containing supernatant having a lysine content of 129.1 g/l, a pH of 6.7, which still comprised 0.5% by volume of cell material, was obtained.

Through the cation-exchange arrangement, at a temperature of 40 to 50° C. and a flow rate of $SV=1\ h^{-1}$, were passed in succession 2300 ml of a 0.66% strength by weight aqueous sulfuric acid, 4800 ml of a 0.882% strength by weight aqueous lysine solution of a pH of 5 and subsequently 1200 ml of a 0.66% strength by weight aqueous sulfuric acid. The pH of the effluent was 5.2. Thereafter, while maintaining the temperature, at an $SV=1\ h^{-1}$, 6200 ml of the aqueous lysine-containing supernatant and then 1100 ml of water were passed through. The effluent was separated off and provided for a pretreatment in a following step. Then, at an $SV=1\ h^{-1}$ at 55° C. 6000 ml of a 4% strength by weight aqueous ammonia solution and subsequently 9100 ml of water were passed through the cation-exchange arrangement.

The results are compiled in tables 1a and 1b. The lysine yield (%) was calculated here as follows:

$$\text{Lysine } e \text{ yield} = \frac{m_{Lys-HCL} \text{ (eluate)}}{m_{Lys-HCL} \text{ (adsorbed)}} \cdot 100 [\%]$$

where $m_{Lys-HCl}$ (eluate): Lys-HCl amount in eluate [g]
$m_{Lys-HCl}$ (adsorbed): amount of Lys-HCl adsorbed to the ion exchanger [g]

TABLE 1a

| Ex. | Effluent for the pretreatment [L per liter of resin] | Lysine feed[1] [g of Lys-HCl per liter of resin] | Sulfuric acid[2] [g/g Lys-HCl] | Ammonia [g/g Lys-HCl] | HDWW [g/g Lys-HCl eluate] | Lysine yield [%] |
|---|---|---|---|---|---|---|
| C1 | — | 210 | 0.7 | 0.305 | 20.5 | 97.5 |
| 1 | 5 | 270 | — | 0.33 | 11.8 | 97.5 |
| 2 | 3 | 150 | — | 0.6 | 12.7 | 97.8 |
| 3 | 3.1 | 270 | — | 0.13 | 11.8 | 97.5 |
| 4 | 1.9 | 150 | — | 0.24 | 12.7 | 97.8 |

[1] Parts by weight of Lys-HCl per liter of cation exchange resin
[2] Sulfuric acid for acidifying the fermentation broth TABLE 1b

| Ex. | Effluent for the pretreatment [L per liter of resin] | Lysine feed [g Lys-HCl per liter of resin] | Sulfuric acid [g/g Lys-HCl] | Ammonia [g/g Lys-HCl] | HDWW [ml/(g-Lys-HCl eluate)] | Lysine yield [%] |
|---|---|---|---|---|---|---|
| 5 | 0.83 | 105.8 | 0.029 | 0.4 | 13.2 | 96.8 |
| 6 | 0.88 | 107.6 | 0.029 | 0.39 | 12.2 | 97.3 |
| 7 | 0.63 | 110.9 | 0.027 | 0.28 | 10.8 | 97.5 |

The invention claimed is:

1. A method for producing a basic amino acid from the fermentation broth of a microorganism strain producing the basic amino acid, the method comprising:
    a) separating the microorganisms from the fermentation broth and
    b) separating the basic amino acid from the aqueous broth obtained in step a) by loading a single-stage or multi-stage arrangement of a strongly acidic cation exchanger in its salt form with the broth obtained in step a) and eluting the basic amino acid,
wherein the aqueous broth, before the loading in step b), has a pH in the range of 4 to 7.5 and at least the first stage of the cation-exchange arrangement is pretreated with an aqueous acid in such a manner that at the end of the pretreatment, the pH at the outlet of the pretreated cation exchanger is of 4.5 to 7.

2. The method according to claim 1, wherein the cation exchanger is pretreated with an aqueous solution of the basic amino acid which has a pH of 4.5 to 7.

3. The method according to claim 2, wherein the aqueous solution of the basic amino acid has a basic amino acid concentration of 1 to 85 g/l.

4. The method according to claim 2, wherein the aqueous solution of the basic amino acid comprises effluent from a loading of the cation-exchange arrangement from a preceding amino acid separation.

5. The method according to one of claims 2, wherein the amount of basic amino acid used for the pretreatment is 0.3 to 1.2 mol per liter of treated ion exchanger.

6. The method according to claim 1, wherein the cation exchanger is treated with a dilute aqueous solution of an acid, the $pK_a$ of which is less than or equal to 4.

7. The method according to claim 6, wherein the dilute aqueous acid solution has an acid concentration in the range of 1 to 20 g/l.

8. The method according to claim 6, wherein the amount of acid equivalents used for the treatment is 0.01 to 0.1 mol per liter of treated ion exchanger.

9. The method according to claim 6, wherein the acid is selected from the group consisting of sulfuric acid, formic acid and hydrochloric acid.

10. The method according to claim 6, wherein, subsequent to the treatment with dilute acid, treatment with a dilute aqueous solution of a basic amino acid is carried out, in which at least 90% of the basic amino acid is present in singly-protonated form.

11. The method according to claim 10, wherein the aqueous solution of the basic amino acid comprises effluent from a loading of the cation-exchange arrangement from a preceding amino acid separation.

12. The method according to claim 1, wherein the acid groups of the ion exchanger before the treatment are present in the form of ammonium or sodium salt groups.

13. The method according to claim 1, wherein the pH of the broth before the loading is 4.0 to 6.0, or the pH is adjusted by adding an acid if outside the pH range of 4.0 to 6.0.

14. The method according to claim 1, wherein the basic amino acid is eluted with aqueous ammonia or sodium hydroxide solution.

15. The method according to claim 1, wherein the basic amino acid is lysine.

16. The method according to claim 1, wherein the cation exchanger arrangement comprises at least two series-connected cation exchanger stages.

17. The method according to claim 1, wherein the cation exchanger is loaded at temperatures of 30 to 60° C.

18. The method according to claim 1, further comprising the isolation of the basic amino acid from the eluate by crystallization.

19. The method according to claim 18, wherein the basic amino acid is eluted with aqueous ammonia, the eluate is concentrated, and the resultant condensate is at least partially recirculated to the elution of the basic amino acid in a subsequent amino acid separation.

20. The method according to claim 1, wherein loading and elution are performed downward.

* * * * *